United States Patent [19]

Israel et al.

[11] Patent Number: 4,973,675
[45] Date of Patent: Nov. 27, 1990

[54] HYBRID NITROSOUREIDOANTHRACYCLINES HAVING ANTITUMOR ACTIVITY

[75] Inventors: Mervyn Israel; Ramakrishnan Seshadri, both of Germantown, Tenn.

[73] Assignee: University of Tennessee Research Center, Knoxville, Tenn.

[21] Appl. No.: 338,031

[22] Filed: Apr. 13, 1989

[51] Int. Cl.$^5$ .......................................... C07H 15/24
[52] U.S. Cl. ...................................................... 536/6.4
[58] Field of Search .......................................... 536/6.4

[56] References Cited

PUBLICATIONS

No. 1047, Doxorubicin (DOX) Analogs Bearing Chemically Reactive Substituents, D. Farquhar, B. S. Andersson, J. E. Zuckerman and R. A. Newman, The University of Texas System Cancer Center, M. D. Anderson Hospital, Houston, Tex. 77030, Proceedings of AACR, vol. 28, Mar. 1987, p. 265.

Doxorubicin Bearing Chemically Reactive Substituents, Authors: D. Farquhar, B. S. Andersson, and R. A. Newman, The University of Texas System Cancer Center, M. D. Anderson Hospital, Houston, Tex. 77030, Investig. New Drugs, 5:115,1987, Article 9.17, p. 115.

*Primary Examiner*—Johnnie R. Brown
*Assistant Examiner*—Elli Peselev
*Attorney, Agent, or Firm*—Luedeka, Hodges & Neeley

[57] ABSTRACT

N-2-chloroalkyl nitrosouredio derivatives of anthracycline-based compounds having antitumor activity are disclosed. Relative to the clinically-used drugs adriamycin and daunorubicin, substantially enhanced antitumor activity against parent murine P388 leukemia and an adriamycin-resistant P388 leukemia subline has been found for the N-2-chloroethylnitrosoureido derivatives of adriamycin, daunorubicin and epirubicin. Chemical stability has been found to be enhanced when employing the 4'-epi stereoisomeric family of these compounds.

7 Claims, 5 Drawing Sheets

HYBRID NITROSOUREIDOANTHRACYCLINES HAVING ANTITUMOR ACTIVITY

This invention was made with government support under Grant Nos. 5-RO1-CA37082 and 5-RO1-CA37209 awarded by the National Cancer Institute. The government has certain rights in this invention.

This invention was made in the course of work supported by research grants from the National Cancer Institute, National Institutes of Health, U.S. Public Health Service and is subject to certain rights owned by the U.S. Government.

The present invention relates to compounds that exhibit certain antitumor activity. The compounds of this invention are related to the anthracycline antibiotics adriamycin (doxorubicin), daunorubicin and epirubicin and comprise hybrid nitrosoureidoanthracyclines and therapeutic compositions containing the same which exhibit unexpectedly high antitumor activity and low toxicity, especially against adriamycin-resistant strains of murine P388 leukemia, and/or enhanced chemical stability.

Adriamycin and daunomycin (the former differs from the latter in having a hydroxyl group in the 14-position) and related compounds are referenced in U.S. Pat. No. 4,610,977. In such patent, there are also references to various related compounds, all of which references, including U.S. Pat. No. 4,610,977, are incorporated herein by reference.

Because of its broad spectrum of activity, the anthracycline antibiotic adriamycin (doxorubicin) has been of major importance in cancer chemotherapy since its clinical introduction in the early 1970's. However, considerations of toxicity, lack of effectiveness against a number of common carcinomatous tumors (e.g. large cell lung, colorectal, and bladder cancer), and development of resistance to adriamycin by initially-sensitive tumors, with collateral resistance to other antitumor agents (phenotypic multidrug resistance), have prompted a continuing search for compounds with improved therapeutic efficacy.

Contrary to certain beliefs heretofore held in the art, the present inventors have discovered that one critical factor among the anthracycline-based antitumor agents as relates to their cytoxicity concerns the ability of the agent to demonstrate some degree of DNA intercalation. Evidence has been found that points to a major mechanism of adriamycin cytotoxicity as involving DNA strand breakage due to drug-mediated inhibition of DNA topoisomerase II, an essential cellular enzyme associated with the topological control of double-stranded DNA synthesis and repair. Whereas it can not be stated categorically that such mode of attack is fully responsible for the observed antitumor effects, it is strongly felt that such is the case.

Accordingly, in the present invention there is provided a class of therapeutically effective compounds of a hybrid nature in that they contain, within a single molecule, two structural features associated with clinical and experimental antitumor activity. Specifically, in each of the compounds of the present invention there is provided an anthracycline system and a nitrosourea alkylating functionality, such compounds being embodied in a group of 2-chloro-alkyl substituents in the alkylating functionality. As will appear more fully hereinafter, certain compounds of the group exhibit good chemical stability while maintaining equal or improved cytotoxicity relative to adriamycin and/or daunomycin, certain compounds exhibit unexpectedly high antitumor activity against certain tumors, and/or, certain compounds exhibit high cytotoxicity with respect to adriamcycin-resistant tumors. The compounds of the present invention are those having the following formula:

where X=Y=H and Z=OH, or Y=H and X=Z=OH, or X=Y=OH and Z=H, and R is a 2-monochloro alkyl substituent having between 2 and 4 carbon atoms.

Figure 1:
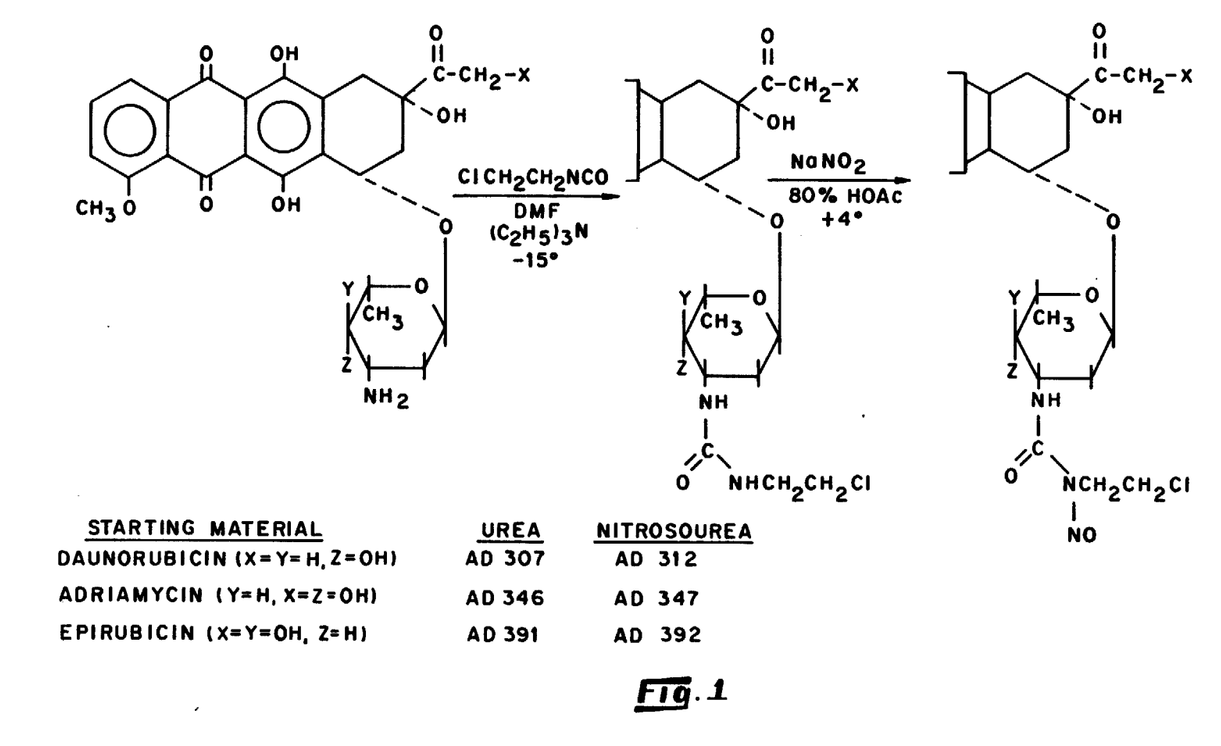
FIG. 1 is a representation of one mode of synthesis of the compounds of the present invention.

The inventors' approach to synthesis of 2-chloroethylnitrosoureidodaunorubicin (Code No. AD 312) and 2-chloroethylnitrosoureidoadriamycin (AD 347) is shown in FIG. 1. The two-step process is applied to the parent antibiotics, taking advantage of the available amino group on the glycoside moiety. Thus, daunorubicin and adriamycin hydrochloride salts, dissolved in cold dimethyl formamide, were treated with a stoichiometric equivalent of 2-chloroethylisocyanate in the presence of triethylamine as an acid acceptor. The resulting chloroethylurea derivatives were then nitrosated at +4° by means of sodium nitrite in 80% aqueous acetic acid. The initially-formed anthracycline ureas were purified by column chromatography prior to nitrosation or use in bioassays; the nitrosation products were homogeneous, as derived from the reaction mixtures.

Figure 2:
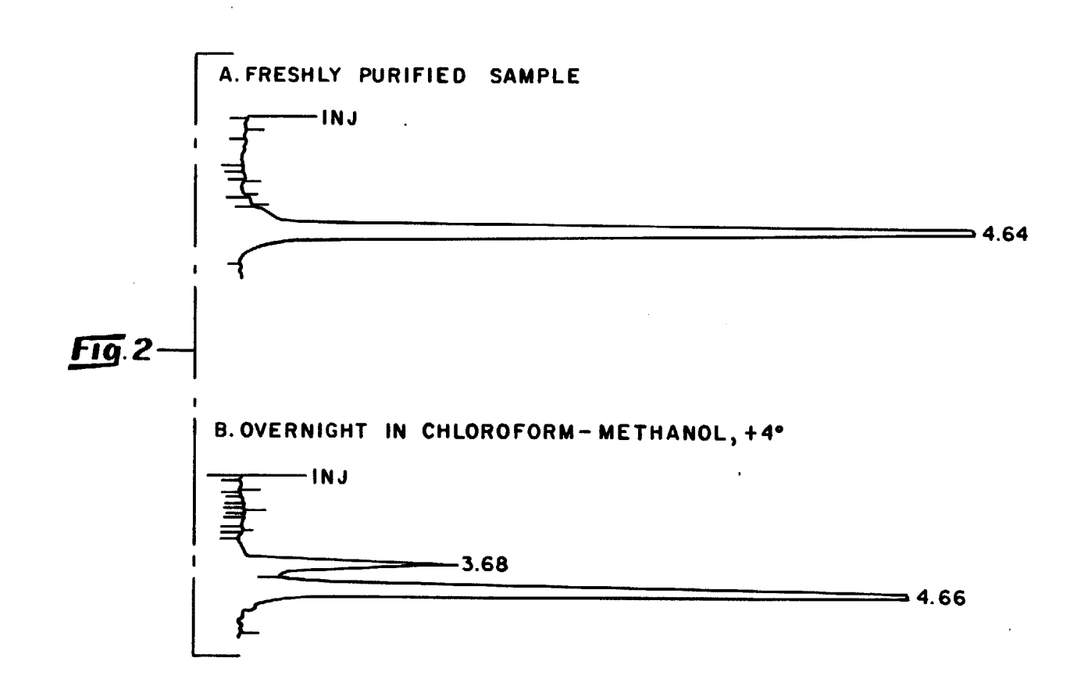
FIGS. 2A and 2B are reproductions of HPLC printouts showing autodegration of N-2-chloroethylnitrosoureidoadriamycin.

In connection with structure-activity analyses, a number of related anthracycline alkyl- and aryl- ureas and -nitrosoureas were prepared following the same two-step synthetic process, except for replacement of 2-chloroethylisocyanate by the appropriate alkyl- or aryl-isocyanate starting material. Details concerning structure, yield, chromatographic behavior, molecular formula, and microchemical analysis for the products derived from daunorubicin and adriamycin are given in Table 1. In some instances, nitrosation of certain urea precursors, afforded products which proved too unstable to isolate in pure form and to characterize. In one instance, no evidence of nitrosation was observed.

substituent ($COCH_3$ from daunorubicin; $COCH_2OH$ from adriamycin), these materials were found to undergo autodegradation. For example, as seen in FIGS. 2A and 2B, a freshly-purified sample of the adriamycin chloroethylnitrosourea product, AD 347, showed a single sharp signal on high performance liquid chromatographic analysis; after standing overnight in chloroform-methanol solution in the cold, a second signal was clearly evident when the solution was examined

TABLE 1

DAUNORUBICIN AND ADRIAMYCIN UREAS AND NITROSOUREAS
PHYSICAL AND CHEMICAL DATA

| Code No. | X | Y | Yield, % | TLC, Rf (Solvent)[a] | HPLC[b] RT, min | Molecular Formula | Analysis[c] |
|---|---|---|---|---|---|---|---|
| Urea Derivatives | | | | | | | |
| AD 305 | H | $CONHCH_3$ | 86 | 0.37 (A) | 4.30 | $C_{29}H_{32}N_2O_{11}$ | C,H,N |
| AD 306 | H | $CONHCH_2CH_3$ | 86 | 0.45 (A) | 4.61 | $C_{30}H_{34}N_2O_{11}$ | C,H,N |
| AD 308 | H | $CONHCH_2CH_2CH_3$ | 81 | 0.50 (A) | 5.11 | $C_{31}H_{36}N_2O_{11}$ | C,H,N |
| AD 328 | H | $CONHCH(CH_3)_2$ | 85 | 0.50 (A) | 5.11 | $C_{31}H_{36}N_2O_{11}$ | C,H,N |
| AD 307 | H | $CONHCH_2CH_2Cl$ | 78 | 0.49 (A) | 5.20 | $C_{30}H_{33}ClN_2O_{11}$ | C,H,Cl,N |
| AD 309 | H | $CONHC_6H_5$ | 81 | 0.52 (A) | 6.24 | $C_{34}H_{34}N_2O_{11}$ | C,H,N |
| AD 330 | H | $CONHC_6H_4\text{-}p\text{-}OCH_3$ | 82 | 0.50 (A) | 6.11 | $C_{35}H_{36}N_2O_{12}$ | C,H,N |
| AD 332 | H | $CONHC_6H_4\text{-}p\text{-}F$ | 76 | 0.49 (A) | 6.42 | $C_{34}H_{33}FN_2O_{11}$ | C,H,F,N |
| AD 334 | H | $CONHC_6H_4\text{-}\underline{m}\text{-}CF_3$ | 78 | 0.54 (A) | 7.19 | $C_{35}H_{33}F_3N_2O_{11}$ | C,H,F,N |
| AD 336 | H | $CSNHCOOCH_2CH_3$ | 75 | 0.78 (A) | 6.44 | $C_{31}H_{34}N_2O_{12}S$ | C,H,N,S |
| AD 342 | OH | $CONHCH_3$ | 72 | 0.50 (B) | 3.54 | $C_{29}H_{32}N_2O_{12}$ | C,H,N |
| AD 344 | OH | $CONHCH_2CH_3$ | 72 | 0.55 (B) | 3.84 | $C_{30}H_{34}N_2O_{12}$ | C,H,N |
| AD 348 | OH | $CONHCH_2CH_2CH_3$ | 76 | 0.57 (B) | 4.30 | $C_{31}H_{36}N_2O_{12}$ | C,H,N |
| AD 350 | OH | $CONHCH(CH_3)_2$ | 84 | 0.56 (B) | 4.23 | $C_{31}H_{36}N_2O_{12}$ | C,H,N |
| AD 346 | OH | $CONHCH_2CH_2Cl$ | 91 | 0.55 (B) | 4.34 | $C_{30}H_{33}ClN_2O_{12}$ | C,H,N[d] |
| AD 391[e] | OH | $CONHCH_2CH_2Cl$ | 60 | 0.55 (B) | 4.48 | $C_{30}H_{33}ClN_2O_{12}$ | C,H,N |
| AD 352 | OH | $CONHC_6H_5$ | 76 | 0.61 (B) | 5.35 | $C_{34}H_{34}N_2O_{12}$ | C,H,N |
| AD 354 | OH | $CONHC_6H_4\text{-}p\text{-}OCH_3$ | 80 | 0.65 (B) | 5.20 | $C_{35}H_{36}N_2O_{13}$ | C,H,N |
| AD 356 | OH | $CONHC_6H_4\text{-}p\text{-}F$ | 83 | 0.65 (B) | 5.51 | $C_{34}H_{33}FN_2O_{12}$ | C,H,F,N |
| AD 360 | OH | $CSNHCOOCH_2CH_3$ | 73 | 0.89 (B) | 5.60 | $C_{31}H_{34}N_2O_{13}S$ | C,H,N,S |
| Nitrosourea Derivatives | | | | | | | |
| AD 310 | H | $CON(NO)CH_3$ | 86 | 0.68 (A) | 6.13 | $C_{29}H_{31}N_3O_{12}$ | C,H,N |
| AD 311 | H | $CON(NO)CH_2CH_3$ | 90 | 0.70 (A) | 6.45 | $C_{30}H_{33}N_3O_{12}$ | C,H,N |
| AD 313 | H | $CON(NO)CH_2CH_2CH_3$ | 89 | 0.78 (A) | 7.02 | $C_{31}H_{35}N_3O_{12}$ | C,H,N |
| AD 312 | H | $CON(NO)CH_2CH_2Cl$ | 86 | 0.75 (A) | 6.80 | $C_{30}H_{32}ClN_3O_{12}$ | C,H,Cl,N |
| AD 343 | OH | $CON(NO)CH_3$ | 82 | 0.69 (B) | 5.40 | $C_{29}H_{31}N_3O_{13}$ | C,H,N |
| AD 345 | OH | $CON(NO)CH_2CH_3$ | 82 | 0.72 (B) | 5.62 | $C_{30}H_{33}N_3O_{13}$ | C,H,N |
| AD 349 | OH | $CON(NO)CH_2CH_2CH_3$ | 80 | 0.78 (B) | 6.56 | $C_{31}H_{35}N_3O_{13}$ | C,H,N |
| AD 347 | OH | $CON(NO)CH_2CH_2Cl$ | 81 | 0.73 (B) | 5.71 | $C_{30}H_{32}ClN_3O_{13}$ | C,H,Cl,N |
| AD 392[e] | OH | $CON(NO)CH_2CH_2Cl$ | 72 | 0.74 (B) | 5.95 | $C_{30}H_{32}ClN_3O_{13}$ | C,H,Cl,N |
| Oxazolidinone degradation products | | | | | | | |
| AD 362 | H | | [f] | 0.20 (A) | 5.28 | $C_{28}H_{27}NO_{11}$ | C,H,N |
| AD 363 | OH | | [f] | 0.35 (B) | 3.44 | $C_{28}H_{27}NO_{12}$ | C,H,N |

[a]Silica gel GF plates, 250 μ. Solvent system: A, chloroform-methanol, 9:1 by volume; B, chloroform-methanol-water, 85:15:1.5 by volume
[b]Phenyl-RADIAL/PAK column (Waters Associates); linear gradient 32% to 65% acetonitrile vs. ammonium formate buffer, pH 4.0, in 6 minutes; flow rate 3.5 ml/min; fluorescence detection, 482 nm excitation wavelength, 550 nm emission cut-off filter; RT = retention time
[c]Unless otherwise indicated, found values are within ±0.4% of theory for the indicated elements.
[d]Cl, calculated 5.24; found 5.70
[e]Product derived from epirubicin; see FIG. 1 for structure.
[f]Recovered from various product auto-degradation reactions.

Notably, there was observed an inherent chemical instability of the urea and nitrosourea products. To a greater or lesser extent, depending upon the particular alkyl or aryl urea substituent and the C-9 chromophore under the same analytical conditions as before. Again, depending upon the specific compound, similar results were seen when compounds were exposed to aqueous media or even maintained in the dry state in a vacuum desiccator. Of importance, all daunorubicin urea and nitrosourea products, regardless of the specific alkyl or aryl substituent, afforded the same anthracycline degradation product; similarly, all adriamycin ureas and nitrosoureas afforded the same other degradation material. This auto-degradation has been found to be associated with the loss of a portion of the alkyl- or aryl-urea and nitrosourea function, leaving behind a common anthracycline component characterized as the corresponding oxazolidinone.

To decrease the auto-degradation activity of the urea and nitrosourea products, the present inventors have found that use as the starting material for the two-step synthesis process of a compound which has a stereochemistry that decreases the proximity of the 4'-hydroxyl function to the adjacent 3'-ureido function will produce a urea and/or nitrosourea which exhibits little tendency to decompose to oxazolidinone, relative to the corresponding adriamycin-derived products. Epirubicin (4'-epiadriamycin) is an example of such a starting material. As noted hereinafter, AD 347 (from adriamycin) and AD 392 (from epirubicin) exhibit almost identical in vitro biological properties. Thus, products of the 4'-epi configuration, with their improved chemical stability, exhibit like antitumor activity, both relative to AD 347; making AD 392 of importance with regard to pharmaceutics.

In the synthesis of the compounds of the present invention, column chromatography was done on Biosil A silicic acid (100–200 mesh, Biorad Laboratories, Richmond. Calif.). IR spectra were recorded on a Perkin-Elmer Model 1320 spectrophotometer as KCl pellets; all compounds exhibited characteristic anthracycline absorption signals at 3500 (OH), 1715–1730 (C=O), 1620, 1580 (quinone) cm$^{-1}$ UV-VIS spectra were recorded in methanol on a Perkin-Elmer Lambda 3B spectrophotometer; quantitative spectral data provided for the compounds AD 312, AD 347, and AD 392 are typical for all of the products disclosed herein. NMR spectra were recorded on a Varian EM-360L cw spectrometer, with tetramethyl-silane as internal standard; the data provided herein for AD 312, AD 347 and AD 392 are characteristic for all the products disclosed herein with regard to the anthracycline-glycoside system. Elemental analyses afforded found values within ±0.4% of theory, unless otherwise indicated herein.

In the synthesis of 2-chloroethylnitrosoureidodaunorubicin (AD 312), 2chloroethylureidodaunorubicin was first synthesized by stirring daunorubicin hydrochloride (225 mg, 0.40 mmol) in dimethyl formamide (5 ml) and triethylamine (0.17 ml) at −15° C. (carbon tetrachloride - dry ice bath). 2Chloroethylisocyanate (40 μl) was added and stirring was continued for 15 minutes, at the end of which time the reaction was complete, as evidenced by the formation of a single product based on thin layer and high performance liquid chromatographic evidence. Dimethyl formamide was removed under high vacuum and the residue was precipitated from chloroform-petroleum ether. After filtration, the material was purified by chromatography on Biosil A (15 g). Elution with chloroform containing 2% methanol afforded pure product (198 mg, 78%); homogeneous on TLC and HPLC. Fifty milligrams (0.079 mmole) of 2-chloroethylureidodaunorubicin thus obtained was stirred in ice-cold (+4°) 80% aqueous acetic acid (2.5 ml). Sodium nitrite (50 mg, 0.59 mmol) was added and stirring was continued for 1 hour. The reaction mixture was then diluted with ice-water (15 ml) and the solid, which separated, was removed by filtration, washed with water (4×10 ml), and dried under high vacuum at room temperature overnight. The product (45 mg, 86%) was homogeneous on TLC and HPLC. NMR (CDCl$_3$); δ1.30 (d, J=6 Hz, 3H, 5'-CH$_3$), 2.40 (s, 3H, COCH$_3$), 4.03 (s, 3H, ArOCH$_3$), 5.22 (bs,1H, 7-H), 5.50 (bs, 1H, 1'-H), 7.12–8.03 (m, 3H, Ar-H), 13.25 (s, 1H, phenolic OH), 14.03 (s, 1H, phenolic OH) ppm; UV-VIS λ max (e) ϵ 233 (40,120), 250 (28,990), 477 (11,940), 494 (11,910), 528 (6400) nm.

In the synthesis of 2-chloroethylnitrosoureidoadriamycin (AD 347), 2-chloroethylureidoadriamycin was first prepared by stirring adriamycin hydrochloride (103 mg, 0.18 mmol) in dimethyl formamide (3 ml) with triethylamine (80 μl), for 5 minutes at −15° C. (carbon tetrachloride - dry ice bath). 2-Chloroethylisocyanate (20 μl 0.201 mmol) was added, and the progress of the reaction was followed by HPLC for the disappearance of starting material and formation of a single product. The reaction was stopped after 20 minutes and dimethyl formamide was removed on a rotary evaporator under high vacuum. The residue was precipitated from chloroform-petroleum ether, washed several times with petroleum ether, and dried overnight under high vacuum at room temperature; yield 105 mg (91%), homogeneous on TLC and HPLC. The 2-chloroethylureidoadriamycin thus prepared (100 mg, 0.154 mmol) was stirred at ±4° (ice bath) in 80% aqueous acetic acid (2.5 ml). Sodium nitrite (100 mg, 1.18 mmol) was added and the mixture was stirred in the cold for 2 hours. The reaction mixture was then diluted with water (20 ml) and the solid product was separated by filtration, washed with water (4×10 ml), and dried at room temperature under high vacuum. Yield was 85 mg (81%); homogeneous on TLC and HPLC. NMR (CDCl$_3$): δ 1.30 (d, J=6 Hz, 3H, 5'—CH$_3$), 4.07 (s, 3H, Ar—OCH$_3$), 4.77 (S, 2H, 14—CH$_2$), 5.28 (bs, 1H, 7—H), 5.55 (bs, 1H, 1'—H), 7.22–8.08 (m, 3H Ar—H), 13.17 (s, 1H phenolic OH), 14.05 (s, 1H, phenolic OH) ppm: UV-VIS: λ max (ϵ) 232 (39,950), 250 (28,170), 477 (11,730), 494 (11,700), 528 (6,400) nm.

Synthesis of 2-chloroethylnitrosoureidoepirubicin (AD 392) was carried out in a manner similar to that for AD 312 and AD 347, with nitrosation of 2-chloroethylureidoepirubicin (8 mg, 0.012 mmol) affording 6 mg (72%) of AD 392, homogeneous on TLC and HPLC. NMR and UV-VIS spectral data were essentially the same as for AD 347.

Certain of the compounds disclosed herein are essentially insoluble in water or saline solution, especially AD 312, AD 337 and AD 392, the solubility of these latter compounds in water being of the order of <25 μg/ml. Accordingly, the compounds are formulated for administration by dissolving the compound in a pharmaceutically acceptable non-toxic carrier which contains a surfactant. The present inventors employ a formulation of 10% Cremaphor EL (a polyhydroxylated castor oil derivative) available from BASF Chemicals, 10% ethanol and 80% aqueous media (sterile water or saline solution). That quantity of the compound desired for establishing an effective dose is dissolved in a 1:1 mixture of Cremaphor EL and ethanol. Thereafter, sufficient aqueous medium is added with stirring to develop a final formulation containing 80% aqueous medium. This formulation is administered parenterally.

Initial assessment of biological activity for the newly-synthesized compounds involved determination of the concentration of agent required to inhibit the growth of human CEM leukemic lymphocytes suspension cultures by 50% following 48 hours of continuous drug exposure, as compared with untreated control cultures ($ID_{50}$ value). Culture and bioassay conditions were as described in Cancer Chemotherapy Pharmacology 20:277 (1987) "Comparative Effects of Adriamycin and DNA-nonbinding Analogues on DNA, RNA, and Protein Synthesis in Vitro", Israel et al., except that cell counts were determined by hemocytometer rather than by automated cell counting. The results of such determinations are shown in Tables 2 and 3. Table 2 shows that a number of the newly-synsthesized products, and in particular AD 312, AD 347, and AD 392, exhibit moderate to marked growth inhibitory activity; in this system $ID_{50}$ values <1.0 μM are considered to be significant. Table 3 compares the growth-inhibitory effects of the three most important compounds of the present invention (AD 312, AD 347, and AD 392) with those of the clinically-used parent antibiotic substances from which they were derived; as seen here, while AD 312 was somewhat less active, AD 347 and AD 392 were 10-fold more potent compared to adriamycin. Table 3 further shows the results of clonogenic assays with cultured murine L1210 leukemia cells wherein AD 347 and AD 392 were again found to be ctive and essentially equipotent with respect to the concentration of drug needed to kill 90% of clonogens following brief (1 hour) cellular drug exposure. In this system, AD 312 was the most potent of the six agents compared.

TABLE 2

In vitro growth-inhibitory activity of anthracycline ureas and nitrosoureas, and related compounds, vs. cultured CEM leukemic lymphocytes.*

| Urea Derivatives | | Nitrosourea Derivatives | |
|---|---|---|---|
| Code No. | $ID_{50}$, μM | Code No. | $ID_{50}$, μM |
| AD 305 | 2.3 | AD 310 | 1.4 |
| AD 306 | >1.0 | AD 311 | 1.5 |
| AD 308 | >5.0 | AD 313 | >1.0 |
| AD 328 | >1.0 | AD 312 | 0.09 |
| AD 307 | 0.30 | AD 343 | 0.48 |
| AD 309 | >1.0 | AD 345 | 0.61 |
| AD 330 | >1.0 | AD 349 | 0.43 |
| AD 332 | >1.0 | AD 347 | 0.005 |
| AD 334 | 0.83 | AD 392 | 0.005 |
| AD 336 | 0.60 | Oxazolidinone | |
| AD 342 | 2.0 | Degradation Products | |
| AD 344 | 0.58 | Code No. | $ID_{50}$, μM |
| AD 348 | 0.77 | AD 362 | 0.88 |
| AD 350 | 0.72 | AD 363 | 0.71 |
| AD 346 | 0.09 | | |
| AD 352 | 0.40 | | |
| AD 354 | 0.71 | | |
| AD 356 | 1.14 | | |
| AD 360 | 0.36 | | |
| AD 391 | 0.08 | | |

*48 hr. continuous drug exposure

TABLE 3

Comparative in vitro growth-inhibitory and cytotoxic activity of the 2-chloroethylnitrosoureido derivatives of daunorubicin, adriamycin, and epirubicin relative to anthracycline parent drugs.

| Drug | CEM, $ID_{50}$ μM* | L1210 $LD_{90}$, μM+ |
|---|---|---|
| Daunorubicin | 0.03 | 0.9 |
| Adriamycin | 0.055 | 0.31 |
| Epirubicin | 0.03 | 0.43 |
| AD 312 | 0.09 | 0.26 |
| AD 347 | 0.005 | 0.58 |
| AD 392 | 0.005 | 0.53 |

*50% growth-inhibitory concentration; suspension culture assay, 48 hr. continuous drug exposure.
+Dose killing 90% of clonogens, 1-hr. drug exposure.

Tables 4–6 present in vivo antitumor data for the 2-chloroethylnitrosoureidodaunorubicin compound (AD 312) against parent sensitive (P388/S) and adriamycin-resistant (P388/ADR) murine P388 leukemias. Assays were run essentially according to the established protocols of the U.S. National Cancer Institute (Geran et al., 1972 "Protocols for Screening Chemical Agents and Natural Products Against Animal Tumors and Other Biological Systems" (3rd Ed.), Cancer Chemotherapy Rep. [3]33, 1–103.), with the test agent given at 3–5 incremental dose levels in each screening experiment and with median survival of treated groups referenced against data for untreated controls. Animal weights were recorded on day 0 and day 7; a net mean percent reduction in weight of 10% or greater for a dose group, or a 10% or greater reduction in survival compared to controls, is taken as an indication of drug toxicity.

Table 4 provides a summary of 4 separate therapy trials with AD 312 vs. P388/S leukemia. In each experiment, untreated control animals showed a median survival of 10 days, with significant increase in weight on day 7 due to build-up of leukemic cell-laden ascites fluid in the peritoneal cavity. Initial studies utilized a multiple dose schedule, with drug administered once daily on days 1, 2, 3 and 4. On this schedule, the highest doses of AD 312 applied (17.5 mg/kg/day) produced 100% 60-day survival without evidence of drug toxicity. The marked activity of AD 312 in this system has been confirmed in multiple separate experiments. At the termination of the experiments, surviving animals were sacrificed and subjected to autopsy; no evidence of tumor or other abnormalities was observed on gross examination.

Additional studies were done with AD 312 vs. murine P388/S under more demanding conditions of assay. As seen in Table 5, using the same size tumor cell inoculum as before, treatment of tumor-bearing animals with a single nontoxic dose of AD 312 (40.5 mg/kg) on day 1 afforded a significant antitumor effect (100% 60-day survival). Furthermore, even when treatment was delayed until day 3 (a model of advanced leukemia), a single 40.5 mg/kg dose of drug proved to be curative to 6 of 7 animals, with the lone death occurring on day 45.

TABLE 4

N-2-Chloroethylnitrosoureidodaunorubicin (AD 312); in vivo antitumor activity vs. murine P388 leukemia[a]

| Dose mg/kg qd 1-4 | Net Mean Percent Weight Change, day 7 | Range of Deaths, days (dying animals) | Median Survival day | Median Increase in Lifespan, % | Long-term Survivors (day of sacrifice)[b] |
|---|---|---|---|---|---|
| 0 (Control) | +15 | 9-13 | 10[c] | — | 0/62 |
| 0.5 | +13 | 10-11 | 11 | +10 | 0/7 |

TABLE 4-continued

N-2-Chloroethylnitrosoureidodaunorubicin (AD 312);
in vivo antitumor activity vs. murine P388 leukemia[a]

| Dose mg/kg qd 1-4 | Net Mean Percent Weight Change, day 7 | Range of Deaths, days (dying animals) | Median Survival day | Median Increase in Lifespan, % | Long-term Survivors (day of sacrifice)[b] |
|---|---|---|---|---|---|
| 1.0 | +6 | 11-18 | 12 | +20 | 0/7 |
| 2.0 | +7 | 12-14 | 13 | +30 | 0/7 |
| 2.7 | +4 | 16-17 | 16 | +60 | 0/7 |
| 4.0 | +2 | 15-20 | 17.5 | +75 | 0/7 |
| 6.0 | +4 | 19-24 | 21 | +110 | 0/7 |
| 9.0 | -2 | 24-35 | 35 | +250 | 3/7 (43) |
| 10.0 | -1 | 38 | | >+500 | 5/7 (60) |
| 11.0 | +1 | 28 | | >+500 | 5/6 (60) |
| 12.5 | ±0 | 35-40 | | >+540 | 4/7 (64) |
| 15.0 | -1 | 32-39 | | >+540 | 4/7 (64) |
| 17.5 | -1 | | | >+540 | 6/6 (64) |

[a]Summary results of 4 separate experiments. B6D2F1 males; 1 × 10$^6$ tumor cell inoculum ip day 0; treatment ip. Historical results for daunorubicin on this protocol, optimal dose 2.0 mg/kg, +75 — +100% ILS, no long-term survivors; for adriamycin, optimal dose 3.0 mg/kg, +150 — +200% ILS, infrequent long-term survivors.
[b]No evidence of tumor or other abnormalities on gross examination.
[c]Identical result achieved in each of 4 separate experiments.

TABLE 5

Activity of N-2-Chloroethylnitrosoureidodaunorubicin (AD 312)
vs. murine P388 leukemia in vivo: special studies[a]

| Dose, mg/kg | Treatment Schedule | Net Mean Percent Weight change, day 7 | Range of Death, days (dying animals) | Median Survival, day | Median Increase in Lifespan, % | Long-term Survivors (day of sacrifice) |
|---|---|---|---|---|---|---|
| Controls | | +8 | 9-12 | 10 | — | 0/13 |
| 12.0 | day 1 only | +6 | 16-22 | 20 | +100 | 0/7 |
| 18.0 | day 1 only | +7 | 18-35 | 31 | +210 | 1/7 (60) |
| 27.0 | day 1 only | +9 | 23-33 | 33 | +230 | 3/7 (60) |
| 40.5 | day 1 only | -3 | | | >+500 | 7/7 (60) |
| Controls | | +15 | | 10 | — | 0/11 |
| 27.0 | day 3 only | +17 | 12-49 | 31 | +210 | 0/7 |
| 40.5 | day 3 only | -4 | 45 | | >+500 | 6/7 (60) |

[a]B6D2F1 males; 1 × 10$^6$ tumor cell inoculum ip day 0; treatment ip.

Table 6 shows the marked activity of AD 312 against a subline of P388 made resistant to adriamycin. This tumor line, originally developed by Johnson et al. (1976), has been reported to be insensitive to adriamycin in vivo and cross-resistant to daunorubicin and various other anthracycline agents. The in vivo lack of response of this tumor to adriamycin and daunorubicin (0% increase in life span) has been confirmed (data for daunorubicin shown in Table 6). In contrast, a single nontoxic dose of AD 312 (40.5 mg/kg) on day 1 afforded a significant therapeutic effect in mice bearing this tumor. When administered once daily for 4 days, AD 312 proved to be 100% curative at each of 3 dose levels spanning the range from 15.0 to 20.0 mg/kg/day. This high activity of AD 312 vs. the P388/ADR tumor is believed to be indicative of the dual mechanistic nature of the drug. The normally adriamycin-sensitive parent P388/S tumor is known to contain high levels of DNA topoisomerase II, whereas the P388/ADR subline contains lower enzyme content, a factor which may relate to the drug-resistant properties exhibited by these cells. As suggested by in vitro alkaline elution filter assay and DNA crosslinking assay data, AD 312 appears to be acting against the parent sensitive tumor via both topoisomerase inhibition and alkylation, whereas against the resistant subline, with its lower levels of topoisomerase II, the contribution of alkylating activity may be more important for the overall antitumor effect.

TABLE 6

Comparative antitumor activity of daunorubicin (DNR) and N-2-chloroethylnitrosoureidodaunorubicin
(AD 312) in vivo vs. murine P388/adriamycin-resistant leukemia*

| Drug | Dose, mg/kg (schedule) | Net Mean Percent Weight change, day 7 | Range of Death, days (dying animals) | Median Survival, day | Median Increase in Lifespan, % | Long-term Survivors (day of sacrifice) |
|---|---|---|---|---|---|---|
| Single Dose | | | | | | |
| 0 (control) | | +17 | 10-13 | 10 | — | 0/11 |
| DNR | 12.0 (d1 only) | -13 | 9-11 | 10 | 0 | 0/7 |
| | 15.0 (d1 only) | -13 | 8-11 | 10 | 0 | 0/7 |
| | 18.0 (d1 only) | -28 | 6-9 | 8 | -20** | 0/7 |
| AD 312 | 27.0 (d1 only) | +5 | 19,26 | | >+500 | 5/7 (60) |
| | 40.5 (d1 only) | -0.5 | 13,27 | | >+500 | 5/7 (60) |
| Multiple Doses | | | | | | |
| 0 (control) | | +2 | 10-12 | 11 | — | 0/19 |
| DNR | 1.0 (qd 1-4) | +20 | 11-12 | 12 | +9 | 0/6 |
| | 2.0 (qd 1-4) | -0.5 | 11-12 | 11 | 0 | 0/7 |
| | 3.0 (qd 1-4) | -7 | 10-12 | 11 | 0 | 0/7 |
| | 4.0 (qd 1-4) | -7 | 9-12 | 10 | -9 | 0/7 |
| AD 312 | 15.0 (qd 1-4) | -4 | | | >+500 | 7/7 (60 |

TABLE 6-continued

Comparative antitumor activity of daunorubicin (DNR) and N-2-chloroethylnitrosoureidodaunorubicin (AD 312) in vivo vs. murine P388/adriamycin-resistant leukemia*

| Drug | Dose, mg/kg (schedule) | Net Mean Percent Weight change, day 7 | Range of Death, days (dying animals) | Median Survival, day | Median Increase in Lifespan, % | Long-term Survivors (day of sacrifice) |
|---|---|---|---|---|---|---|
|  | 17.5 (qd 1-4) | −9 |  |  | > +500 | 7/7 (60) |
|  | 20.0 (qd 1-4) | −9 |  |  | > +500 | 7/7 (60) |

Figure 3:
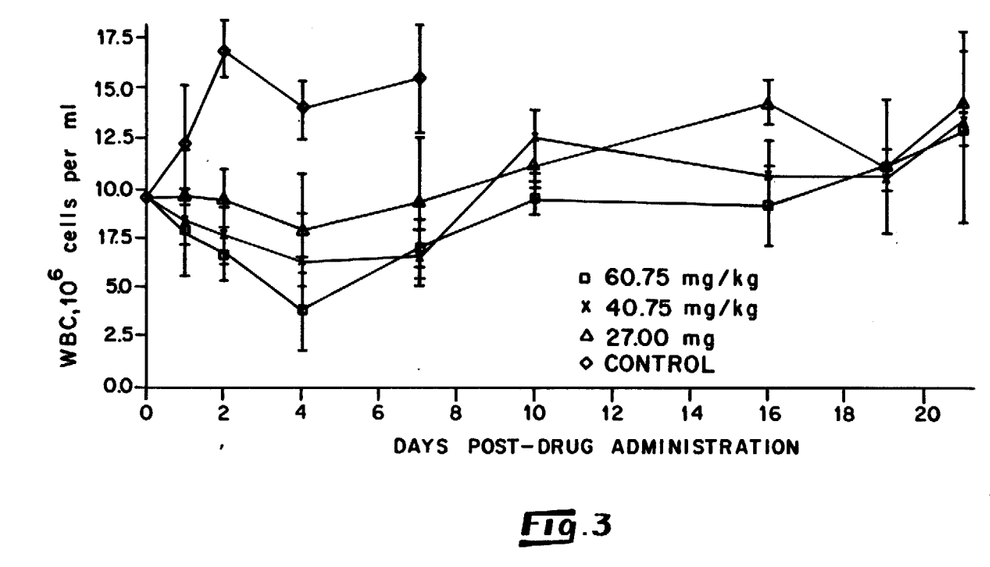
FIG. 3 is a graphic representation of white blood cell counts in mice following a single dose of 2-chloroethyl-nitrosoureidodaunorubicin.

*B6D2F1 males; 1 × 10⁶ tumor cell inoculum ip day 0; treatment ip.day 1 only. Origin of tumor line: R. K. Johnson, A. A. Ovejera, and A. Goldin, Cancer Treatment Rep., 60: 99–102, 1976.
**Toxic Notable in these therapy experiments is the lack of toxicity at the curative dose levels achieved with AD 312. Clinically and in laboratory animals, anthracycline antibiotics and chloroethylnitrosourea alkylating agents currently used in medical oncology are known to be strongly myelosuppressive, with the effects of the alkylating agents on suppression of bone marrow activity being particularly profound and long-lasting. No such effect appears to be present in tumor-bearing animals treated with AD 312. Furthermore, in hematotoxicity studies with non-tumor-bearing animals of the same strain as used in the therapy trials, a single 40.5 mg/kg dose of AD 312 produced only a modest lowering of the white blood cell count, from a median of $9 \times 10^6$ cells/ml before drug administration to a nadir on day 4 of $6 \times 10^6$ cells/ml, with full recovery by day 10 (FIG. 3). Even a dose of AD 312 of 60.75 mg/kg, 1.5 times that of the curative therapeutic single dose, was still not at an acute toxic level (about 67% reduction in white blood cell count on day 4), with rapid recovery again being achieved. No significant change in red blood cells counts was seen at either of the 3 dose levels of AD 312 employed in these experiments.

As seen in Table 7, comparable results to those with AD 312 are seen with AD 347 vs. murine P388/S (e.g. 16.0 mg/kg/day×4, > 500% increase in life span, 57% survival at 60 days).

into relaxed forms. Accordingly, this assay is taken as the definitive test of drug-DNA intercalation.

Drugs were tested at 4 concentrations over a 125-fold concentration range. As described below, adriamycin, used as positive control, showed a concentration-dependent ability to interfere with the conversion of supercoiled DNA to relaxed forms. Similar effects were seen with the chloroethylnitrosourea products AD 312 and AD 347 under the assay conditions, thus establishing the ability of these compounds to intercalate, a prerequisite for toposiomerase II inhibition. Furthermore, based upon data obtained from the evaluation of a large number of anthracycline structural variants by means of this assay, an arbitrary scale for the expression of the relative strength of drug-DNA intercalation has been suggested. On this scale (0 for no intercalation, 9 for very strong intercalation), the parent anthracycline agents daunorubicin, adriamycin, and epirubicin were each assigned a value of 7, indicating a strong effect. In comparison, AD 312 was assigned a value of 5 (strong intercalation, but not quite of the order of adriamycin), while AD 347 was accorded a value of 8. It should also be noted that AD 307 and AD 346 were found by this assay to be reasonably strong intercalators. These compounds are 2-chloroethylurea derivatives of daunorubicin and adriamycin, respectively (i.e. not nitrosoureas, but chemical intermediates from which the nitrosoureas

TABLE 7

N-2-Chloroethylnitrosoureidoadriamycin (AD 347); in vivo antitumor activity vs. murine P388 leukemia*

| Dose, mg/kg qd 1-4 | Net Mean Percent Weight Change, day 7 | Range of Deaths, days (dying animals) | Median Survival day | Median Increase in Lifespan, % | Long-term Survivors (day of sacrifice) |
|---|---|---|---|---|---|
| 0 (control) | +15 | 10-13 | 10 | — | 0/15 |
| 2.0 | +8 | 16-18 | 17 | +70 | 0/7 |
| 4.0 | +2 | 18-21 | 19 | +90 | 0/7 |
| 8.0 | +2 | 19-24 | 22 | +120 | 0/7 |
| 12.0 | +2 | 22-37 | 26 | +160 | 2/7 (60) |
| 16.0 | −3 | 26-31 |  | > +500 | 4/7 (60) |

*B6D2F1 males; 1 × 10⁶ tumor cell inoculum ip day 0; treatment ip.

With the demonstration of high in vitro and in vivo antitumor activity, a number of biochemical studies have been undertaken with certain of these agents to examine the possible mechanistic basis for their action. The results of these studies clearly establish the DNA topoisomerase II-inhibitory activity and alkylating activity of AD 312, AD 347, and AD 392.

DNA unwinding assays were used to measure the ability of a test drug to interfere with DNA topoisomerase I-mediated unwinding of plasmid PC15 supercoiled DNA. DNA topoisomerase I controls the topology of double-stranded DNA and is itself not inhibited by DNA intercalating agents. Rather, intercalating agents cause distortion of the torsional angle between adjacent DNA strand components and thereby interfere with the ability of topoisomerase I to convert supercoiled DNA were derived).

Figure 4A:
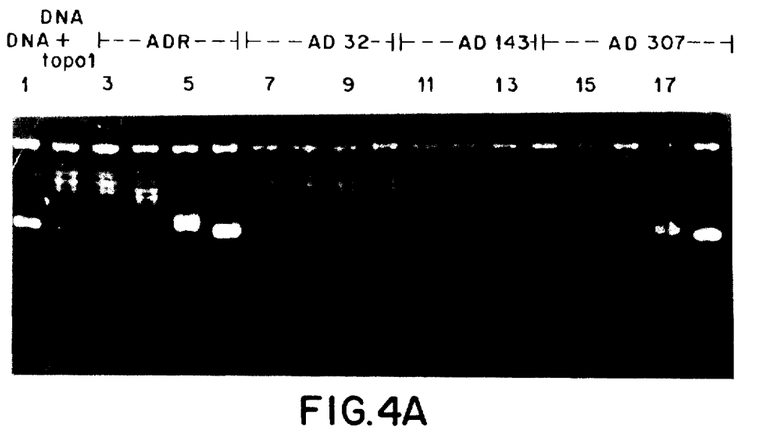
FIGS. 4A and 4B are a photographic reproduction of the results of DNA unwinding assays performed on various compounds, including compounds of the present invention.
Figure 4B:
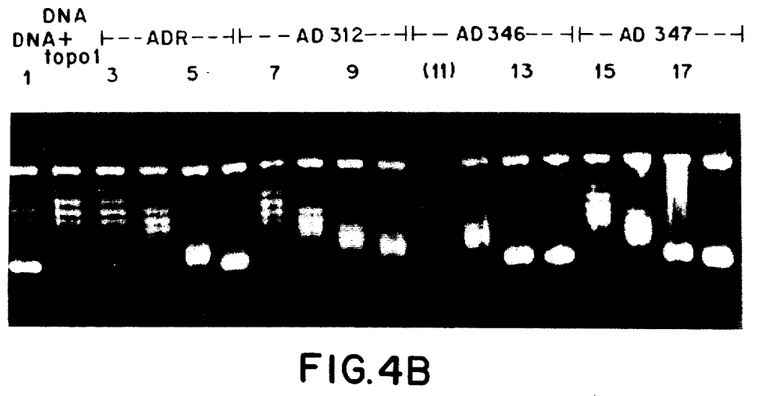

Lane 1 in FIGS. 4A and 4B, shows a mixture of supercoiled and relaxed PC15 DNA in the absence of enzyme. Lane 2 (enzyme control) shows the disappearance of the supercoiled DNA form, and its conversion, under the influence of topoisomerase I, to intermediate and fully relaxed forms. Lanes 3-6, FIGS. 4A and 4B, show the ability of increasing concentrations of adriamycin (positive control) to interfere with the conversion of supercoiled DNA to relaxed forms. Lanes 7-10 and 15-18, FIG. 4B, document the corresponding effects of the chloroethylnitrosourea products AD 312 and AD 347 in this assay. Thus, the ability of these compounds to intercalate, a prerequisite for topoisomerase II inhibition, is clearly established.

Figure 5A:
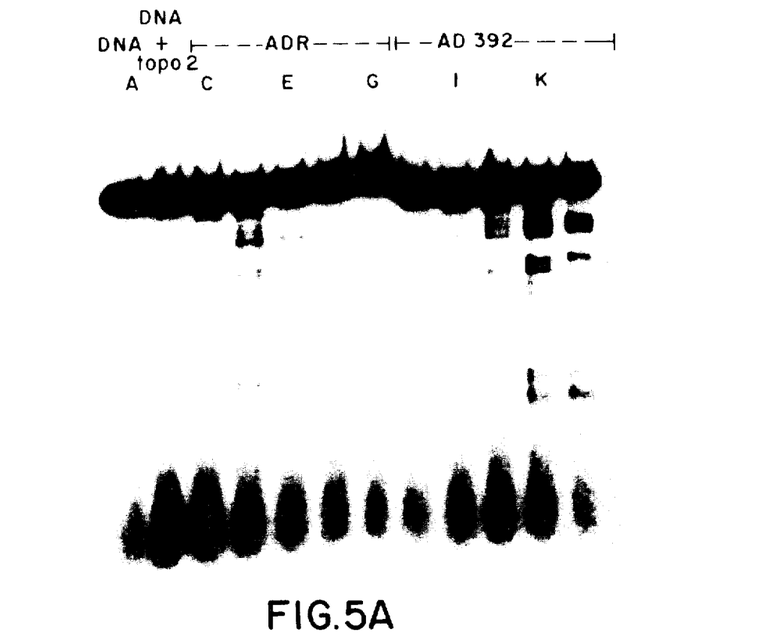
FIGS. 5A and 5B are a photographic reproduction of the results of drug-stimulated topoisomerase II-mediated DNA cleavage assays performed on various compounds, including compounds of the present invention.
Figure 5B:
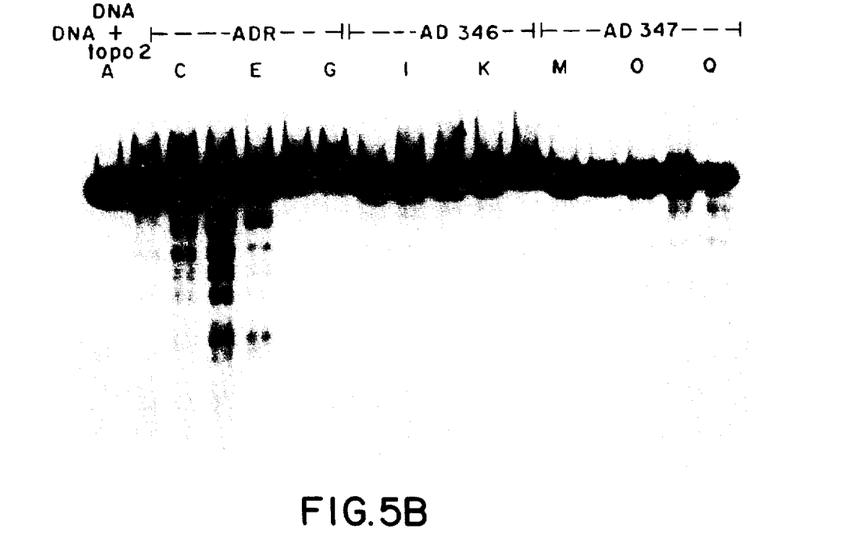

DNA intercalation is a necessary but not a sufficient requirement for DNA topoisomerase II-mediated DNA cleavage. Accordingly, determination of drug-induced enzyme inhibition requires direct assay with isolated topoisomerase II. These assays involve determination of drug-enhanced topoisomerase II-mediated cleavage of PMC41 DNA appropriately end-labeled with [α—$^{32}$P-]dATP. Results of these assays are shown in FIGS. 5A and 5B. As better seen in FIG. 5B, lane B, purified topoisomerase II, under the assay conditions, causes fragmentation of the DNA (background cleavage), as indicated by the radioautographic appearance of bands of cleaved DNA having differing mass values. When assayed over a 625-fold concentration range, at low concentrations adriamycin enhances DNA fragmentation, while at concentrations of 4.6 μM (2.5 μg/ml) and higher background cleavage is eliminated (lanes C-G, FIGS. 5A and 5B; this curious behavior probably reflects some drug-DNA saturation process for adriamycin which is not clearly understood. The chloroethylnitrosoureas AD 347 (lanes M-Q, FIG. 5B) and AD 392 (lanes H-L, FIG. 5A;) show similar enhancement of DNA cleavage with increasing concentrations, thus conclusively establishing AD 347 and AD 392 to be inhibitors of DNA topoisomerase II. In contrast to adriamycin, however, no saturation of background cleavage is seen with these agents over the concentration range employed. Notable also is the effect of urea derivatives AD 346 (lanes H-L, FIG. 5B) and AD 391, which, despite being strong intercalators, do not enhance topoisomerase II-mediated cleavage (i.e. do not inhibit the enzyme).

By means of the DNA alkaline elution filter assay technique, it is possible to assess the nature of damage induced in DNA by exposure to drugs and other agents. Depending on the assay conditions, DNA lesions can be quantified as direct strand breaks, DNA-DNA interstrand crosslinks, and protein-associated strand breaks and crosslinks. The action of akylating-type drugs on DNA typically results in a predominant formation of direct DNA single-strand breaks and DNA-DNA crosslinks. DNA intercalating agents show a preponderance of protein-associated DNA damage, detectable as protein-associated single-strand breaks and DNA-protein crosslinks.

The nature of nitrosoureidoanthracycline-induced DNA damage in murine L1210 and human CLL lymphocytes was assessed by means of the alkaline elution filter technique. Results of these assays are given in Table 8. Murine L1210 leukemic lymphocytes, like P388/S lymphocytes, are known to contain high levels of topoisomerase II. In these cells, adriamycin, a known DNA intercalator/topoisomerase II inhibitor, produces significant amounts of protein-associated single-strand breaks, without producing much in the way of direct strand breaks and DNA-DNA interstrand cross-links, as seen with alkylating agents. In contrast, AD 347 and AD 392 produce a pattern of DNA damage consistent with both topoisomerase II inhibition and DNA-alkylating action.

TABLE 8

| | | DNA interaction in murine L1210 (high topoisomerase II content) and human CLL (low topoisomerase II content) lymphocytes* | | | | | | | |
|---|---|---|---|---|---|---|---|---|---|
| | Time after treatment, | L1210 | | | | CLL | | | |
| Drug | hr | DB | PAB | DD-CL | DP-CL | DB | PAB | DD-CL | DP-CL |
| Adriamycin | 0 | −0.1 | <u>1.0</u> | 0.1 | <u>0.5</u> | 0.1 | 0.1 | 0.0 | 0.1 |
| AD 347 | 0 | <u>1.4</u> | <u>1.4</u> | <u>0.2</u> | <u>0.7</u> | <u>1.8</u> | <u>0.2</u> | −0.18 | 0.16 |
| | 1 | | | | | <u>2.0</u> | <u>0.2</u> | −0.04 | 0.17 |
| | 3 | | | | | <u>2.0</u> | <u>0.3</u> | <u>0.35</u> | 0.19 |
| AD 392 | 0 | <u>0.7</u> | <u>0.9</u> | <u>0.4</u> | <u>0.4</u> | | | | |

*All concentrations 1 μM, 1-hr incubation. Each entry represents the mean of at least two experiments, frequency per 10$^6$ nucleotides; statistically significant increase above back-ground underlined. DB, direct (non-enzymatic) DNA breaks; PAB, protein-associated DNA cleavage; DD-CL, interstrand DNA crosslinks; DP-CL, DNA-protein cross-links.

B-cell type lymphocytes freshly obtained from patients with chronic lymphocytic leukemia (CLL) show undetectable levels of topoisomerase II. On alkaline elution assay, protein-associated DNA damage caused by adriamycin cannot be detected in these cells to any significant level; nor is there any meaningful drug-induced DNA damage of the direct strand break of interstrand crosslink type. AD 347, in contrast, continues to show some level of protein-associated DNA damage in these cells, but also affords significant levels of alkylation-type damage, seen as direct strand breaks and, with increasing time, DNA interstrand crosslinks. These results suggest a use of AD 347, or a related nitrosoureidoanthracycline, against human B-cell CLL.

To further assess the alkylation potential of AD 312, the ability of this agent to form interstrand cross-links in isolated calf thymus DNA was examined using an ethidium bromide fluorescence assay. AD 312 was found to induce appreciable interstrand crosslinks during 4 hours at 50° C., whereas AD 307 at the same concentration (10 mM) appeared to produce no such effect. In one set of experiments, DNA was exposed briefly to AD 312 (30 minutes at 50° C.) before being reisolated by precipitation with ethanol. When this DNA was then incubated further at 50° C. in aqueous solution now free of the drug, crosslinks continued to form for several hours. Such continuing reaction reflects the presence in the DNA of long-lived precursors of crosslinks similar to what has been found for the classical antitumor chloroethylnitrosoureas. The conclusion that AD 312 acts, at least in part, by a mechanism analogous to other chloroethylnitrosoureas is reinforced by the observation that purified O$^6$-alkylguanine-DNA alkyltransferase, when added to AD 312-treated DNA, can block the protracted second step in crosslink formation. It appears, therefore, that AD 312 induces DNA interstrand crosslinks via an initial adduct at O$^6$-guanine.

What is claimed is:

1. Anthracycline derivatives selected from the group having the formula where XY=H and Z=OH, or Y=H and X=Z=OH, or X=Y=OH and Z=H, and R is a 2-monochloroalkyl substituent having between 2 and 4 carbon atoms.

2. The compound as set forth in claim 1 wherein the compound is 2-chloroethylnitrosoureidodaunorubicin.

3. The compound as set forth in claim 1 wherein the compound is 2-chloroethylnitrosoureidoadriamycin.

4. The compound as set forth in claim 1 wherein the compound is 2-chloroethylnitrosoureidoepirubicin.

5. A therapeutic composition exhibiting antitumor activity against murine P388 leukemias in mice, said composition consisting essentially of a pharmaceutically acceptable non-toxic carrier and an effective amount of the compound as claimed in claim 1.

6. A therapeutic composition exhibiting antitumor activity against adriamycin-resistant murine P388 leukemias in mice, said composition consisting essentially of a pharmaceutically acceptable non-toxic carrier and an effective amount of the compound as claimed in either of claims 2, 3 or 4.

7. A 4' epi stereochemical equivalent of 2-chloroethylnitrosoureidodaunorubicin.

* * * * *

UNITED STATES PATENT AND TRADEMARK OFFICE
CERTIFICATE OF CORRECTION

PATENT NO. : 4,973,675
DATED : November 27, 1990
INVENTOR(S) : Mervyn Israel and Ramakrishnan Seshadri It is certified that error appears in the above-identified patent and that said Letters Patent is hereby corrected as shown below:

In the Abstract, line 1, "nitrosouredio" should be --nitrosoureide--.

Column 5, line 49, "2chloroe-" should be --2-chloroe- --.

Column 5, line 54, "2Chloroethylisocyanate" should be --2-Chloroethylisocyanate--.

Column 6, line 11, delete "(e)" and place parenthesis around symbol $\epsilon$.

Column 6, line 19, "(20µ10.201 mmol) should be --20µl, 0.201 mmol--.

Column 6, line 54, "AD 337" should be --AD 347--

Column 16, Claim 1, line 1, "XY" should be --X = Y--.

Signed and Sealed this

Thirtieth Day of June, 1992

*Attest:*

DOUGLAS B. COMER

*Attesting Officer*   *Acting Commissioner of Patents and Trademarks*